(12) United States Patent
Wu et al.

(10) Patent No.: US 9,149,348 B2
(45) Date of Patent: Oct. 6, 2015

(54) INTRA-ORAL SCANNER FOR DIGITAL IMPRESSION AND REAL-TIME RECONSTRUCTION SYSTEM FOR INNER SURFACE TOPOGRAPHIC IMAGE OF ORAL CAVITY

(71) Applicant: SHENZHEN UNIVERSITY, Shenzhen, Guangdong (CN)

(72) Inventors: Qingyang Wu, Guangdong (CN); Bin Hui, Guangdong (CN); Xiangdong Gong, Guangdong (CN); Jingzhen Li, Guangdong (CN); Jianpang Zhai, Guangdong (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 396 days.

(21) Appl. No.: 13/872,072

(22) Filed: Apr. 27, 2013

(65) Prior Publication Data
US 2013/0236850 A1    Sep. 12, 2013

Related U.S. Application Data

(63) Continuation of application No. PCT/CN2011/081243, filed on Oct. 25, 2011.

(30) Foreign Application Priority Data

Oct. 29, 2010   (CN) .......................... 2010 1 0526092

(51) Int. Cl.
| | |
|---|---|
| H04N 9/47 | (2006.01) |
| H04N 7/18 | (2006.01) |
| A62B 1/04 | (2006.01) |
| A61C 9/00 | (2006.01) |
| A61B 1/00 | (2006.01) |
| A61B 1/24 | (2006.01) |
| G01B 11/24 | (2006.01) |

(Continued)

(52) U.S. Cl.
CPC ............. *A61C 9/006* (2013.01); *A61B 1/00172* (2013.01); *A61B 1/24* (2013.01); *G01B 11/24* (2013.01); *A61B 1/04* (2013.01); *A61B 1/0684* (2013.01)

(58) Field of Classification Search
USPC ............... 348/66, 49, 50, 136, 142, 192, 202, 348/203, 207.1, 207.11, 208.11, 224.1, 326, 348/333.1, 360, 381, 500, 661, 671, 743, 348/744, 750, 756; 353/22, 31, 33, 34, 37, 353/49, 61, 72, 78; 382/127, 140, 169, 204, 382/274, 276; 349/68
See application file for complete search history.

(56) References Cited

U.S. PATENT DOCUMENTS 5,410,370 A * 4/1995 Janssen .......................... 348/756
5,863,125 A * 1/1999 Doany ............................ 353/84

(Continued)

*Primary Examiner* — Jefferey Harold
*Assistant Examiner* — Mustafizur Rahman

(57) ABSTRACT

The present invention relates to medical devices and provides an intra-oral scanner for a digital impression. The intra-oral scanner has a window for limiting an acquisition range. The intra-oral scanner sequentially includes, along a light path, a three-color LED light source module, a microlens array sheet, a collimator lens group, a gray coding grating plate, an optical deflector, a projection lens group, a first reflector, a second reflector and a third reflector positioned in parallel with each other with their reflective surfaces opposing to each other, and a camera. The intra-oral scanner can perform a scan directly in the human oral cavity and obtain the digital impression of three-dimensional topography of the tooth and soft tissue in real-time, thereby meeting the requirements of dentists and dental technicians to quickly and accurately obtain the oral impressions.

8 Claims, 1 Drawing Sheet

(51) Int. Cl.
  *A61B 1/04* (2006.01)
  *A61B 1/06* (2006.01)

(56) References Cited
  U.S. PATENT DOCUMENTS 6,256,425 B1 * 7/2001 Kunzman ............... 382/274
  6,266,105 B1 * 7/2001 Gleckman ............... 348/743
  6,520,644 B1 * 2/2003 Lee .......................... 353/31
  2008/0068533 A1 * 3/2008 Yun et al. ................ 349/68
  2009/0076321 A1 * 3/2009 Suyama et al. .......... 600/109
  2010/0117947 A1 * 5/2010 Kim et al. ................ 345/102
  2010/0216086 A1 * 8/2010 Sylvester et al. ........ 433/29

* cited by examiner

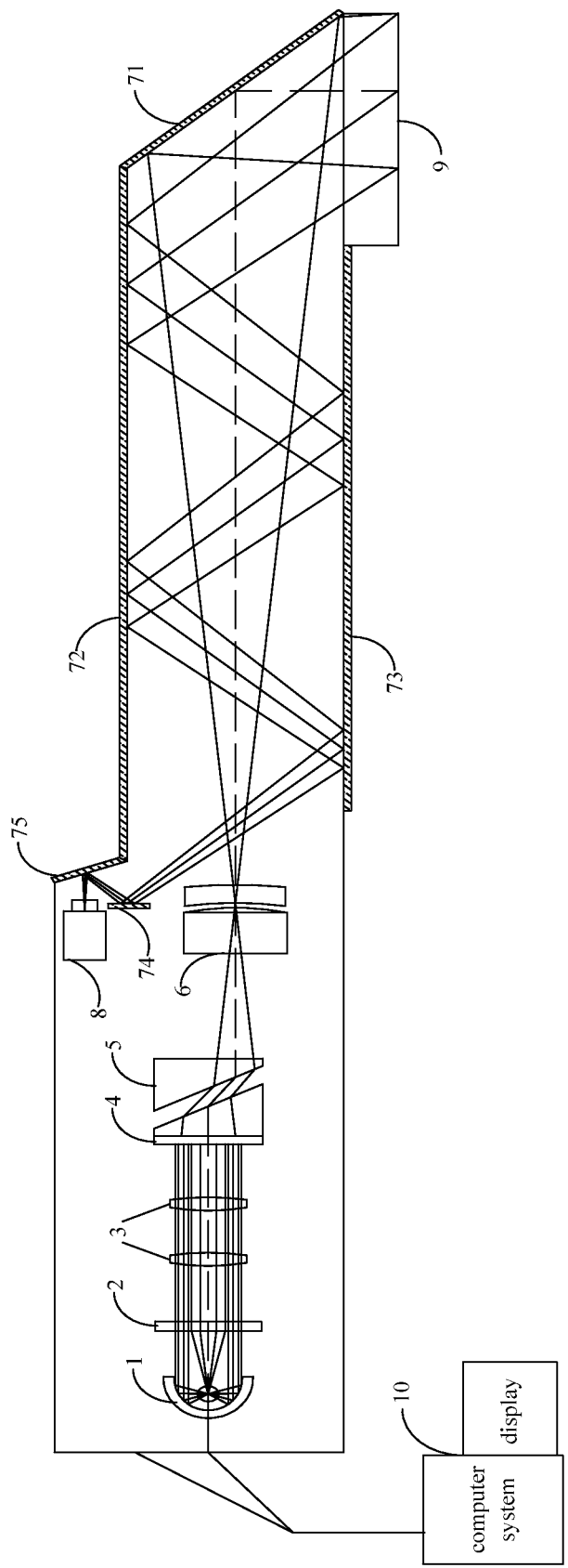

US 9,149,348 B2

INTRA-ORAL SCANNER FOR DIGITAL IMPRESSION AND REAL-TIME RECONSTRUCTION SYSTEM FOR INNER SURFACE TOPOGRAPHIC IMAGE OF ORAL CAVITY

CROSS-REFERENCE TO RELATED APPLICATIONS

This present application is a Continuation Application of PCT application No. PCT/CN2011/081243 filed on Oct. 25, 2011, which claims the benefit of Chinese Patent Application No. 201010526092.9 filed on Oct. 29, 2010; the contents of which are hereby incorporated by reference.

FIELD

The present invention relates to medical devices and, more particularly, to an intra-oral scanner for a digital impression and a real-time reconstruction system for an inner surface topographic image of an oral cavity.

BACKGROUND

Oral impressions are an important information storage source in the clinical dental clinics and repair processes. Almost every patient needs to obtain one or more impressions. By comparing multiple impressions obtained prior to, during, and after treatment, doctors can understand the effect of the treatment, thereby improving the accuracy of the examination, diagnosis and treatment. Dental technicians also need to determine the shape of dentures according to the impressions.

At present, easy operation, high precision, convenient storage digital impression technology is gaining more and more dental medical expert's attention. More and more efforts and funds are put into the research of this technology. Digital impressions may be taken in two manners according to the position of the scan, i.e. extra-oral scan and intra-oral scan. The intra-oral scan is a new scan manner emerging in recent years. In the intra-oral scan, a probe is inserted into the patient's oral cavity to directly measure the teeth to obtain a digital impression in real-time. In comparison with the extra-oral scan, the intra-oral scan has many advantages. Firstly, it improves patient satisfaction. Secondly, to the doctor, the intra-oral scan further improves the quality of the impression, reduces the number of operation steps and operation time, greatly reduces the material consumption and labour force, and provides effective guidance for doctor's operation. Finally and most importantly, it also establishes a communication platform between the patient and doctor, which allows the doctor and patient to discuss the obtained digital impressions. This not only allows the patient to understand his/her disease conditions and the intent of the doctor, but also allows the doctor to better formulate or correct a treatment program based on the needs of the patient, thus making the doctor-patient relationship more harmonious.

Due to the particularity of the real-time intra-oral scan, in addition to the requirement of a compact probe (can be inserted into the oral cavity), it is also required that the scan be as fast as possible. Therefore, it is desired to provide an intra-oral scan technology which can perform a scan directly in the human oral cavity and obtain the scan result in real-time.

SUMMARY

Accordingly, the present invention is to provide an intraoral scanner for digital impressions that can perform a scan directly in the human oral cavity and obtain data of three-dimensional topography of the oral cavity inner surface such as the tooth and soft tissue in real-time.

In one aspect, the present invention provides an intra-oral scanner for a digital impression. The intra-oral scanner has a window for limiting an acquisition range. The intra-oral scanner includes, along a light path, a three-color LED light source module; a microlens array sheet for making distribution of a light beam generated by the three-color LED light source module become uniform; a collimator lens group for collimating the light beam; a gray coding grating plate for generating a gray coding fringe pattern required for projection; an optical deflector for offsetting the light beam such that lights of different wavelengths have different offset distance; a projection lens group for projecting a gray coding grating image passing through the gray coding grating plate and the optical deflector onto a surface of an object to be measured; a first reflector for redirecting the light beam so that the project lights are emitted through the window; a second reflector and a third reflector positioned in parallel with each other with their reflective surfaces opposing to each other for ensuring a long distance transmission of the lights within a limited space; and a camera for imaging, acquiring and recording a fringe distribution on an oral cavity inner surface.

In another aspect, the present invention further provides a real-time reconstruction system for an inner surface topographic image of an oral cavity, comprising the intra-oral scanner described above. The real-time reconstruction system further comprises a computer system and a synchronizing circuit control system. The synchronizing circuit control system controls synchronization of a strobe frequency of the three-color LED light source module with an acquisition frequency of the camera, and the computer system performs a real-time reconstruction of the inner surface topography of the oral cavity according to the fringe images acquired by the intra-oral scanner.

The intra-oral scanner can perform a scan directly in the human oral cavity and obtain the digital impression of three-dimensional topography of the tooth and soft tissue in real-time, thereby meeting the requirements of the dentist and dental technician to quickly and accurately obtain the oral impressions. This technology can achieve accurate phase shift of the fringe image projected onto the surface of the object to be measured by taking advantage of the fact that lights of different wavelengths (colours) have different offset distance. The two parallel flat reflectors are used to extend the light path such that the image outside the window can be transmitted within a small space, which facilitates reducing the overall size of the intra-oral scanner. In addition, the synchronizing circuit is used to synchronize the strobe frequency of three wavelength (colour) lights of the three-color LED light source module with the shutter frequency of the camera, thereby achieving a real-time data acquisition.

Other independent aspects of the invention will become apparent by consideration of the detailed description, claims and accompanying drawings.

BRIEF DESCRIPTION OF THE DRAWINGS

FIG. 1 is a schematic view of a real-time reconstruction system for an inner surface topographic image of an oral cavity according to one exemplary embodiment.

DESCRIPTION OF THE EMBODIMENTS

Before any independent embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In various embodiments of the invention, according to the speed and accuracy requirements of the real-time intra-oral scan and the complicated-shape and uneven-height characteristics of the inner surface of the oral cavity, the intra-oral scanner employs an active projection light field to form an encoded fringe pattern on the tooth surface, and employs an imaging device to record the tooth morphology image carrying the encoded fringe pattern at a location at an angle relative to a projection light path. Position and height information are obtained according to the method of phase-height mapping based on the phase information, thereby achieving real-time reconstruction of surface topography of the tooth and soft tissues around.

FIG. 1 is a schematic view of a real-time reconstruction system for an inner surface topographic image of an oral cavity according to one exemplary embodiment. For convenience of description, only the part relevant to this embodiment is shown.

Referring to FIG. 1, the real-time reconstruction system for an inner surface topographic image of an oral cavity includes a three-color LED light source module 1, a microlens array sheet 2, a collimator lens group 3, a gray encoding grating plate 4, an optical deflector 5, a projection lens group 6, a first flat reflector 71, a second flat reflector 72, a third flat reflector 73, a fourth flat reflector 74, a fifth flat reflector 75, a camera 8, a window 9, and a computer system 10. The three-color LED light source module 1 includes a three-color LED light source and a reflective bowl covering the three-color LED light source. The second flat reflector 72 and the third flat reflector 73 are disposed in parallel with their reflective surfaces opposing to each other. The optical deflector 5 includes a pair of wedge prisms having an identical shape and a right-angled edge.

The three-color LED light source is used to sequentially generate projection lights of different wavelengths (colors), which may be, for example, a red-green-blue three-color LED light source. The projection lights have a uniform distribution after passing through the microlens array sheet 2. The projection lights radiate onto the gray encoding grating plate 4 after being collimated through the collimator lens group 3. The lights transmitted through the gray encoding grating plate 4 carry gray encoded grating information. After the lights are deflected through the optical deflector 5, due to the different wavelengths and different offset distances, the position of the gray encoding fringe pattern formed by the lights finally reflected by the first reflector 71 out of the window 9 and projecting onto the oral cavity inner surface is also shifted, thus forming three fringe image frames with a same phase shift that are required by three-step phase-shifting technology (algorithm).

Then, the camera 8 and the second to fifth flat reflectors image and record the fringe distribution on a reference plane of the oral cavity inner surface or a surface of an object to be measured. The second flat reflector 72 and the third flat reflector 73 are disposed such that their reflective surfaces are parallel to and oppose to each other, which can therefore ensure to transmit the image of the object to be measured outside the window 9 within a relative small space through multiple reflections. The image is then transmitted to the camera 8 by the other two flat reflectors. Fringe images recorded by the camera system are transmitted through a circuit to the computer system 10, and the computer system 10 performs the real-time reconstruction of the inner surface topography of the oral cavity according to the acquired fringe images. In addition, the computer system 10 also employs a synchronizing circuit control system to control a strobe frequency of the multicolor LED light source 1 and an acquisition frequency of the camera 8 to ensure the synchronization therebetween. After the acquisition is completed, the computer system 10 first processes the three phase shift fringe images to extract phase information therefrom. The process is as follows: the computer system 10 first calculates a wrapped phase distribution of the three recorded fringe images according to a formula of the three-step phase shifting; the computer system 10 then unwraps the wrapped phase; finally, the computer system obtains the three-dimensional surface topography data of the oral cavity by reconstruction according to phase-height mapping.

It should be understood that in FIG. 1 the fourth reflector and the fifth reflector can be chosen according to actual needs, as long as the image of the object to be measured carrying the phase modulation information can be captured by the camera 8 after it is redirected by the fourth reflector 74 and/or fifth reflector 75. Specifically, one or both of the fourth reflector 74 and the fifth reflector 75 may be used. It is also to be understood that the fourth reflector 74 and the fifth reflector 75 may be omitted if the camera 8 is at an appropriate location with respect to the second reflector 72 and the third reflector 73.

The above-described intra-oral scanner for a digital impression can be made into the shape of a probe head. The parallel second reflector 72 and the third reflector 73 are spaced less than 16 mm. The optical path is extended through multiple reflections to ensure that the size of the probe's front end inserted into the oral cavity is less than 20 mm ×20 mm. In comparison with other technical solutions, this embodiment provides a projection and imaging system that can achieve a smaller size of the intra-oral scanner while achieving high speed projection and data acquisition resolution, thereby making it suitable for intra-oral operation.

The intra-oral scanner of the embodiment of the present invention can perform a scan directly in the human oral cavity and obtain the digital impression of three-dimensional topography of the tooth and soft tissue in real-time, thereby meeting the requirements of the dentist and dental technician to quickly and accurately obtain the oral impressions.

It will be apparent to those skilled in the art that various modifications and variations can be made to the disclosed structure without departing from the scope or spirit of the invention. In view of the foregoing, it is intended that the present invention cover modifications and variations of this invention provided they fall within the scope of the following claims and their equivalents.

What is claimed is:

1. An intra-oral scanner for a digital impression, the intra-oral scanner having a window for limiting an acquisition range, the intra-oral scanner sequentially includes, along a light path,
   a three-color LED light source module;
   a microlens array sheet for making distribution of a light beam generated by the three-color LED light source module become uniform;
   a collimator lens group for collimating the light beam;
   a gray encoding grating plate for generating a gray encoded fringe pattern required for projection;
   an optical deflector for offsetting the light beam such that lights of different wavelengths have different offset distance;

a projection lens group for projecting a gray encoded grating image passing through the gray encoding grating plate and the optical deflector onto a surface of an object to be measured;

a first reflector for redirecting the light beam so that projection lights are emitted through the window;

a second reflector and a third reflector positioned in parallel with each other with their reflective surfaces opposing to each other for ensuring a long distance transmission of the lights within a limited space; and a camera for imaging, acquiring and recording a fringe distribution on an oral cavity inner surface.

2. The intra-oral scanner according to claim 1, wherein the three-color LED light source module comprises a three-color LED light source and a reflective bowl covering the three-color LED light source.

3. The intra-oral scanner according to claim 1, further comprising, before the camera, a fourth reflector and/or a fifth reflector for redirecting the light beam reflected by the second reflector and the third reflector such that the light beam is able to enter the camera.

4. The intra-oral scanner according to claim 1, wherein the optical deflector comprises a pair of wedge prisms having an identical shape and having a right-angled edge.

5. A real-time reconstruction system for an inner surface topographic image of an oral cavity, comprising an intra-oral scanner according to claim 1, and further comprising a computer system and a synchronizing circuit control system, wherein the synchronizing circuit control system controls synchronization of a strobe frequency of the three-color LED light source module with an acquisition frequency of the camera, and the computer system performs a real-time reconstruction of the inner surface topography of the oral cavity according to the fringe images acquired by the intra-oral scanner.

6. A real-time reconstruction system for an inner surface topographic image of an oral cavity, comprising an intra-oral scanner according to claim 2, and further comprising a computer system and a synchronizing circuit control system, wherein the synchronizing circuit control system controls synchronization of a strobe frequency of the three-color LED light source module with an acquisition frequency of the camera, and the computer system performs a real-time reconstruction of the inner surface topography of the oral cavity according to the fringe images acquired by the intra-oral scanner.

7. A real-time reconstruction system for an inner surface topographic image of an oral cavity, comprising an intra-oral scanner according to claim 3, and further comprising a computer system and a synchronizing circuit control system, wherein the synchronizing circuit control system controls synchronization of a strobe frequency of the three-color LED light source module with an acquisition frequency of the camera, and the computer system performs a real-time reconstruction of the inner surface topography of the oral cavity according to the fringe images acquired by the intra-oral scanner.

8. A real-time reconstruction system for an inner surface topographic image of an oral cavity, comprising an intra-oral scanner according to claim 4, and further comprising a computer system and a synchronizing circuit control system, wherein the synchronizing circuit control system controls synchronization of a strobe frequency of the three-color LED light source module with an acquisition frequency of the camera, and the computer system performs a real-time reconstruction of the inner surface topography of the oral cavity according to the fringe images acquired by the intra-oral scanner.

* * * * *